US00PP25854P3

(12) United States Plant Patent
Schoone

(10) Patent No.: US PP25,854 P3
(45) Date of Patent: Sep. 1, 2015

(54) *PHALAENOPSIS* ORCHID PLANT NAMED 'POPPY HONEY'

(50) Latin Name: *Phalaenopsis hybrida*
Varietal Denomination: Poppy Honey

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 154 days.

(21) Appl. No.: 13/986,345

(22) Filed: Apr. 23, 2013

(65) Prior Publication Data

US 2013/0291263 P1 Oct. 31, 2013

Related U.S. Application Data

(60) Provisional application No. 61/638,033, filed on Apr. 25, 2012.

(30) Foreign Application Priority Data

Apr. 26, 2012 (NL) ..... PBR OPS909

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Poppy Honey' particularly characterized by flowers which are yellow/green with some white in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Poppy Honey'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Poppy Honey'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate. The new *Phalaenopsis* 'Poppy Honey' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Poppy Honey' originated from a cross made by the inventor in 1999 in Strengweg, Heemskerk, The Netherlands. The female or seed parent is the *Phalaenopsis* cultivar designated 'Golden Peoker', unpatented. The male or pollen parent is the *Phalaenopsis* cultivar designated 'Taida Salu', unpatented. The new *Phalaenopsis* 'Poppy Honey' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Poppy Honey', which in combination distinguish this *Phalaenopsis* as a new and distinct cultivar:

1. flowers which are yellow/green with some white in the labellum;

2. plant produces more than one inflorescence;
3. plants may be propagated economically and uniformly using tissue culture;
4. inflorescences are long and sturdy; and
5. relatively short, dark-green foliage.

In comparison with the parental cultivars of 'Poppy Honey', the female parent 'Golden Peoker' has yellow/green flowers with purple spots and the male parent 'Taida Salu' has yellow/green flowers with purple stripes, whereas the flowers of 'Poppy Honey' are yellow/green with only a few grey/purple spots on the sepals.

Presently, the commercial cultivar to which 'Poppy Honey' can be meaningfully compared is '252479' (unpatented). 'Poppy Honey' is a little smaller in size and also the flowers are a little smaller than '252479'. The color of the flowers of '252479' is a little lighter than the color of 'Poppy Honey' and 'Poppy Honey' has some grey/purple spots on the sepals. Also differs the shape of the labellum.

BRIEF DESCRIPTION OF THE PHOTOGRAPHS

The accompanying photographs illustrate the overall appearance of the new *Phalaenopsis* 'Poppy Honey' showing the colors as true as is reasonably possible with colored reproductions of this type. Colors in the photographs may differ slightly from the color values cited in the detailed botanical description, which accurately describe the color of 'Poppy Honey'.

DETAILED BOTANICAL DESCRIPTION

Figure 1:
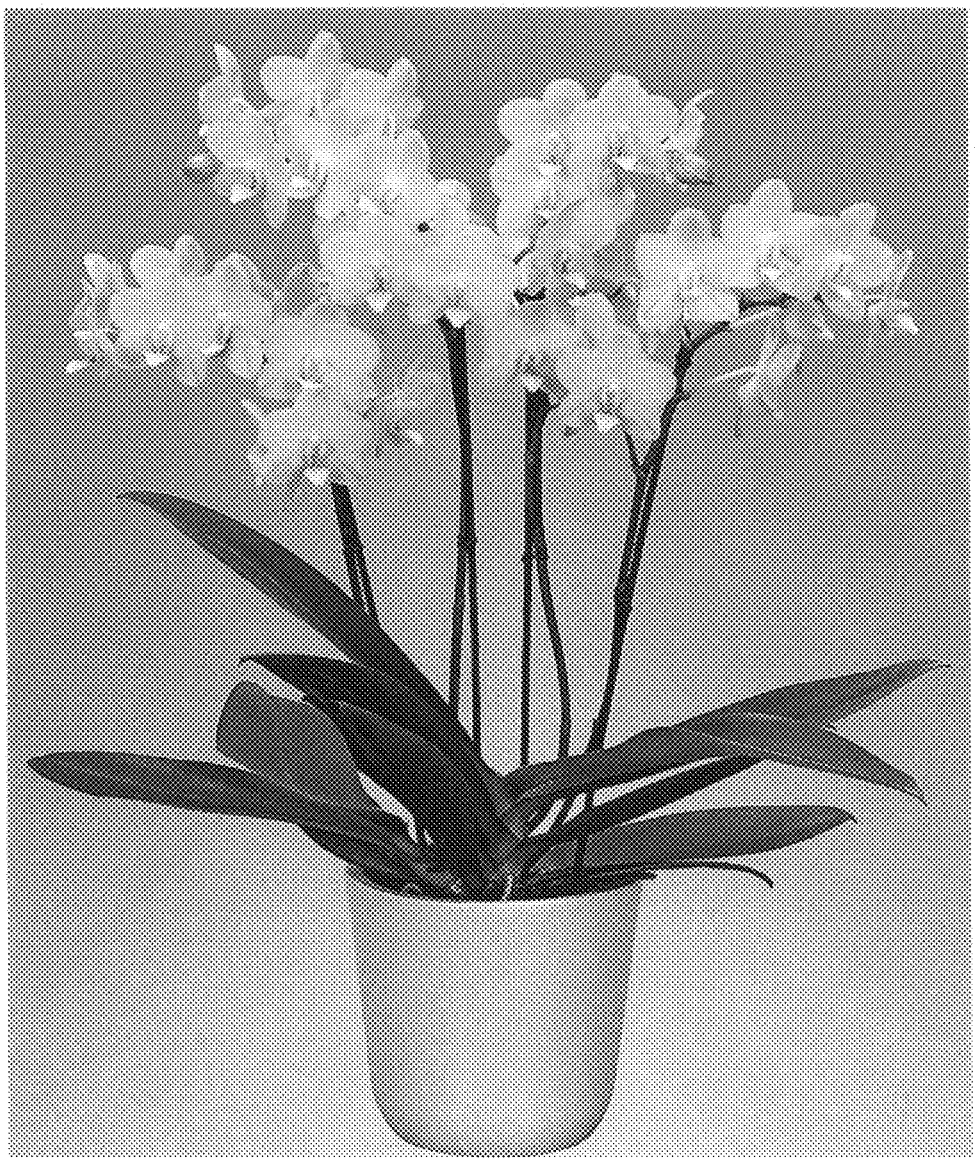
FIG. 1 shows a side view perspective of a typical flowering plant of 'Poppy Honey' in a 12 cm pot, at 16 months of age.

The new *Phalaenopsis* cultivar 'Poppy Honey' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Poppy Honey' as grown in a greenhouse in Strengweg, Heemskerk, The Netherlands, under conditions which closely approximate those generally used in commercial practice. Initially, the ideal temperature to grow plants of 'Poppy Honey' is 27° C. during the day and at night. Then, during the flowering phase of 'Poppy Honey', the ideal growing temperature is 20-22° C. during the day and 18° C. at night. Light levels for growing 'Poppy Honey' are a minimum of 5,000 lux and a maximum of 10,000 lux. A balanced fertilizer with level of 200 ppm N, 87 ppm P, 168 ppm K is applied. Duration of growth of 'Poppy Honey' from potting size is between 10 and 14 months.

Color references are made to The Royal Horticultural Society Colour Chart (RHS), 2007 edition, except where general colors of ordinary significance are used. Color values were taken under daylight conditions at approximately noon in Zaandammerweg, Assendelft, The Netherlands. The age of the 'Poppy Honey' plants described is 12 months after potting.

Classification:

*Botanical.*—*Phalaenopsis hybrida.*

Parentage:

*Female or seed parent.*—*Phalaenopsis* cultivar designated 'Golden Peoker', unpatented.

*Male or pollen parent.*—*Phalaenopsis* cultivar designated 'Taida Salu', unpatented.

Propagation:

*Type.*—Tissue culture.

*Rooting habit and description.*—Fleshy; approximately 4 mm-7 mm wide and green/gray in color (RHS 191B); freely branching. It takes 12 weeks for plants growing in tissue culture to initiate roots.

Plant:

*Size at maturity.*—Height (from bottom of pot to highest flower): about 40 to 45 cm. Spread: about 30 to 40 cm.

*Growth habit.*—Small; dark green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-4 racemes with flowers appear.

Foliage:

*Quantity per plant.*—About 6 to 9 leaves are produced before flowering.

*Arrangement and attachment.*—Half up/horizontal and on two sides.

*Overall shape of leaf.*—Oval, the tip is little pointy and asymmetric.

*Texture (upper & underside).*—Smooth and leathery.

*Pubescence.*—None.

*Mature leaf length.*—About 13 to 21 cm.

*Mature leaf width.*—About 3 to 7 mm.

*Mature leaf thickness.*—About 2 mm.

*Mature leaf color.*—Upper side: green (RHS 137A). Under side: green (RHS 137D).

*Leaf base.*—Acute.

*Margin.*—Entire.

*Venation.*—Pattern: parallel. Color of midvein: upper side: green (RHS N137A). Under side: green (RHS N138A).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 4. Number of flowers per raceme: about 5 to 9. Length: about 34 to 40 cm.

*Peduncle.*—Diameter: about 4 cm. Strength: strong. Aspect: upright. Texture: glabrous and smooth. Color: green (RHS 138B) which runs into yellow/green (RHS 145A).

*Buds.*—Height (from base to tip): about 15 mm. Diameter (at midpoint): about 15 mm. Shape: egg-shaped/oval. Color: main color is yellow/green (RHS 146D) which runs into yellow/green (RHS 146A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-4 racemes appear flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
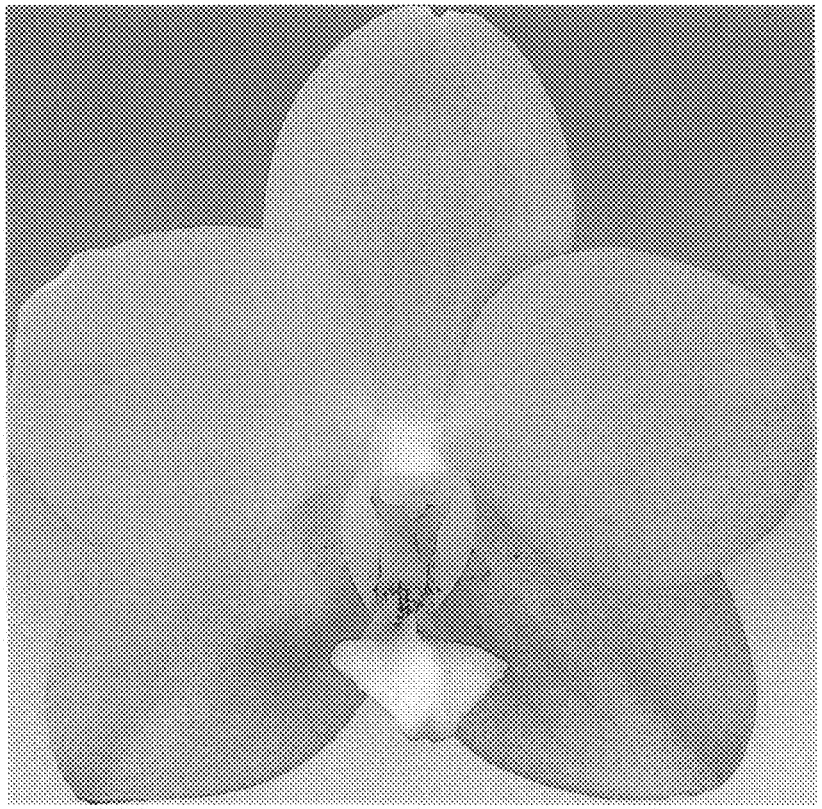
FIG. 2 shows a close-up view of a typical flower of 'Poppy Honey'.
Figure 3:
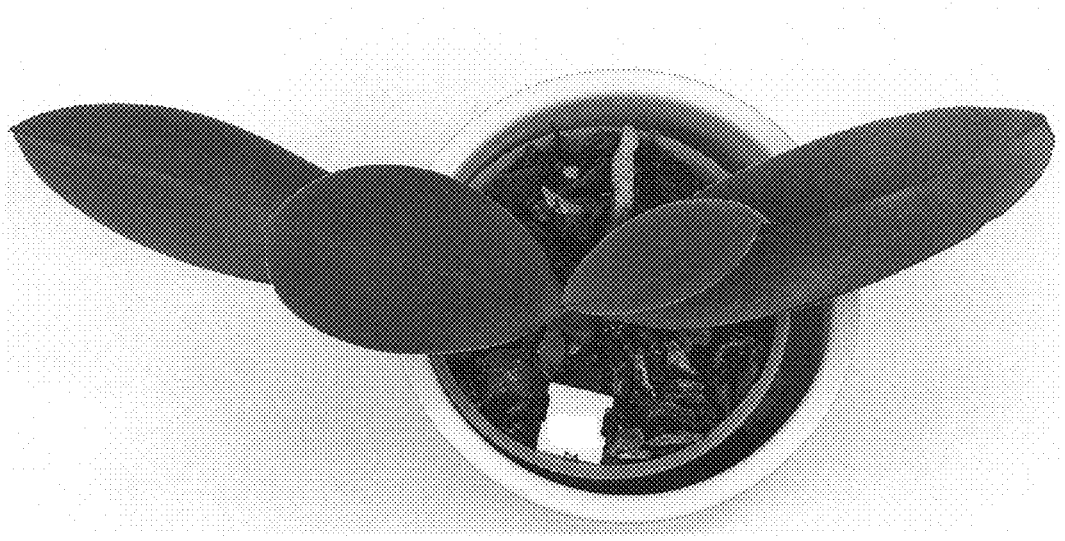
FIG. 3 shows a close-up view of the typical leaves of 'Poppy Honey'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2 Size (of single bloom): Height: about 40 mm to 55 mm. Diameter: about 45 mm to 50 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate, little triangular and weakly cupped. Apex: oval. Margin: entire and weakly undulate. Base: broadly ovate. Length: about 50 mm. Width: about 55 mm. Texture: Upper surface: smooth and satiny. Under surface: smooth and satiny. Color (when fully opened): upper side: Main color is yellow/green (a combination of RHS 154A and RHS 154B) with at the base some white (RHS NN155C). Under side: Main color is yellow/green (RHS 150B) with at the base some white (RHS NN155C). Labellum: Overall Representation: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire. Apex: oval. Length: about 16 mm. Width (not flattened): about 10 mm. Depth of tube created from lateral lobes of labellum: about 3 mm. Texture: Upper and under surface: smooth and satiny. Color (when fully opened): Midlobe: upper surface: from the cirrhi white (RHS NN155C) than yellow (RHS 10A). Close to the base grey/red (RHS 180A) with small grey/red spots (RHS 180A). Under surface: from the cirrhi white (RHS N155A), on the sides red/purple (RHS 71D) which runs into yellow (RHS 5D). Lateral lobes: upper surface: from base yellow (RHS 5A) with red/purple spots (RHS 71D) which runs into white (RHS NN155C). Under surface: white (RHS NN155D). At the edges yellow (RHS 5D). Cirrhi: about 1 mm (2 small points). Color: white (RHS NN155C). Pestle (Callosities): Length: about 3 mm. Width (not flattened): about 1 to 3 mm. Color: yellow (RHS 5A) with grey/purple spots (RHS 185A).

*Sepals*.—Arrangement: Outer whorl comprises 3 sepals, one dorsal and two lateral sepals. Overall shape: oval, undulate and weakly cupped. Margin: entire and weakly undulate. Length: about 29 mm. Width: about 20 mm. Apex: dorsal: oval with small gap; lateral: oval with little point. Texture: Upper and under surface: smooth and satiny. Color (when fully opened): upper side: Dorsal sepal: Main color is yellow/green (RHS 150B) with at the base some white (RHS NN155C). Lateral sepal: main color is yellow/green (RHS 150B). At the base red/purple edge (RHS 70B) and some white (RHS NN155C). Also some grey/purple spots at the base (RHS 185D). Under side: Dorsal sepal: main color is yellow/green (RHS 150B) and in the center haze of RHS 144B. At the base some white (RHS NN155C). Lateral sepals: Main color is yellow/green (RHS 150B) at the base white (RHS NN155C). The vein is green (RHS 138A).

*Pedicel*.—Length: about 28 mm. Diameter: about 3 mm. Texture: glabrous and smooth. Color: close to the flower white (RHS NN155C), in the middle yellow/green (RHS 150B) and then yellow/green (RHS 146B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: white (RHS NN155C). Pollinia: Quantity: two. Diameter: about 1 mm. Color: yellow/green (RHS 21A).

*Ovary*.—Length: about 3 mm. Diameter: about 2 mm. Color: RHS NN155C.

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Poppy Honey', as illustrated and described herein.

* * * * *